(12) United States Patent
Nakamatsu et al.

(10) Patent No.: US 7,833,760 B2
(45) Date of Patent: Nov. 16, 2010

(54) PROCESS FOR THE PRODUCTION OF β-AMINO ACIDS USING ACYLASE

(75) Inventors: Tsuyoshi Nakamatsu, Tokyo (JP); Hisashi Kawasaki, Tokyo (JP); Kunihiko Watanabe, Kawasaki (JP); Masakazu Nakazawa, Kawasaki (JP); Kunisuke Izawa, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 648 days.

(21) Appl. No.: 11/924,760

(22) Filed: Oct. 26, 2007

(65) Prior Publication Data

US 2009/0258398 A1  Oct. 15, 2009

Related U.S. Application Data

(62) Division of application No. 11/198,242, filed on Aug. 8, 2005, now Pat. No. 7,351,571.

(30) Foreign Application Priority Data

Aug. 6, 2004  (JP) .............................. 2004-231306

(51) Int. Cl.
*C12P 13/04* (2006.01)
*C12N 1/20* (2006.01)

(52) U.S. Cl. .................. 435/106; 435/252.1; 435/252.3

(58) Field of Classification Search ........................ None
See application file for complete search history.

(56) References Cited

U.S. PATENT DOCUMENTS

| 6,214,609 | B1 | 4/2001 | Landis et al. |
| 6,893,852 | B1 | 5/2005 | Izui et al. |
| 6,905,819 | B1 | 6/2005 | Matsuzaki et al. |
| 7,244,569 | B2 | 7/2007 | Matsuzaki et al. |
| 2003/0054506 | A1 | 3/2003 | Otsuna et al. |
| 2005/0214912 | A1 | 9/2005 | Nozaki et al. |
| 2006/0263861 | A1 | 11/2006 | Nozaki et al. |
| 2007/0026504 | A1 | 2/2007 | Suzuki et al. |

FOREIGN PATENT DOCUMENTS

| WO | WO98/50575 | 11/1998 |
| WO | WO03/020943 | 3/2003 |
| WO | WO03/080854 | 10/2003 |

OTHER PUBLICATIONS

Gröger, H., et al., "The first aminoacylase-catalyzed enantioselective synthesis of aromatic β-amino acids," Org. Biomol. Chem. 2004;2(14):1977-1978.
Lin, P-H., et al., "Identification and characterization of a new fene from *Variovorax paradoxus* Iso1 encoding N-acyl-D-amino acid amidohydrolase responsible for D-amino acid production," Eur. J. Biochem. 2002;269:4868-4878.
Soloshonok, V.A., et al., "Biocatalytic Approach to Enantiomerically Pure β-Amino Acids," Tetrahedron:Asymmetry 1995;6(7):1601-1610.
European Search Report for EP Appl. No. 05016796.4 (Nov. 7, 2005).
U.S. Appl. No. 11/782,260, filed Jul. 24, 2007, Suzuki et al.

*Primary Examiner*—Delia M Ramirez
*Assistant Examiner*—Younus Meah
(74) *Attorney, Agent, or Firm*—Shelly Guest Cermak; Cermak Nakajima LLP

(57) ABSTRACT

The present invention relates to a *Variovorax* sp. which produces an acylase having an asymmetric hydrolysis activity on an N-acetyl β-amino acid to selectively produce an R-β-amino acid, and a *Burkholderia* sp. which produces both an acylase having an asymmetric hydrolysis activity on an N-acetyl β-amino acid to selectively produce an S-β-amino acid and an acylase having an asymmetric hydrolysis activity of an N-acetyl β-amino acid to selectively produce an R-β-amino acid, and a process for the selective production of an S-, or R-β-amino acid using the above strains.

6 Claims, 1 Drawing Sheet

```
                              SEQUENCE LISTING

<160> NUMBER OF SEQ ID NOS: 2

<210> SEQ ID NO 1
<211> LENGTH: 1526
<212> TYPE: DNA
<213> ORGANISM: Variovorax sp.
<220> FEATURE:
<221> NAME/KEY: 16S rDNA (16Sr RNA)
<222> LOCATION: (1)..(1526)

<400> SEQUENCE: 1
gagtttgatc ctggctcaga ttgaacgctg gcggcatgcc ttacacatgc aagtcgaacg      60
gcagcgcggg agcaatcctg gcggcgagtg gcgaacgggt gagtaataca tcggaacgtg     120
cccaatcgtg ggggataacg cagcgaaagc tgtgctaata ccgcatacga tctacggatg     180
aaagcagggg atcgcaagac cttgcgcgaa tggagcggcc gatggcagat taggtagttg     240
gtgaggtaaa ggctcaccaa gccttcgatc tgtagctggt ctgagaggac gaccagccac     300
actgggactg agacacggcc cagactccta cgggaggcag cagtggggaa ttttggacaa     360
tgggcgcaag cctgatccag ccatgccgcg tgcaggatga aggccttcgg gttgtaaact     420
gcttttgtac ggaacgaaac ggctctttct aataaagagg gctaatgacg gtaccgtaag     480
aataagcacc ggctaactac gtgccagcag ccgcggtaat acgtagggtg caagcgttaa     540
tcggaattac tgggcgtaaa gcgtgcgcag gcggtgatgt aagacagttg tgaaatcccc     600
gggctcaacc tgggaactgc atctgtgact gcatcgctgg agtacggcag aggggatgg      660 aattccgcgt gtagcagtga aatgcgtaga tatgcggagg aacaccgatg gcgaaggcaa     720
tcccctgggc ctgtactgac gctcatgcac gaaagcgtgg ggagcaaaca ggattagata     780
ccctggtagt ccacgcccta aacgatgtca actggttgtt gggtcttcac tgactcagta     840
acgaagctaa cgcgtgaagt tgaccgcctg gggagtacgg ccgcaaggtt gaaactcaaa     900
ggaattgacg gggacccgca caagcggtgg atgatgtggt ttaattcgat gcaacgcgaa     960
aaaccttacc cacctttgac atgtacggaa tttgccagag atggcttagt gctcgaaaga    1020
gaaccgtaac acaggtgctg catggctgtc gtcagctcgt gtcgtgagat gttgggttaa    1080
gtcccgcaac gagcgcaacc cttgtcatta gttgctacat tcagttgggc actctaatga    1140
gactgccggt gacaaaccgg aggaaggtgg ggatgacgtc aagtcctcat ggcccttata    1200
ggtggggcta cacacgtcat acaatggctg gtacaaaggg ttgccaaccc gcgaggggga    1260
```

```
gctaatccca taaaaccagt cgtagtccgg atcgcagtct gcaactcgac tgcgtgaagt    1320
cggaatcgct agtaatcgtg gatcagaatg tcacggtgaa tacgttcccg ggtcttgtac    1380
acaccgcccg tcacaccatg ggagcgggtt ctgccagaag tagttagctt aaccgcaagg    1440
agggcgatta ccacggcagg gttcgtgact ggggtgaagt cgtaacaagg tagccgtatc    1500
ggaaggtgcg gctggatcac ctcctt                                        1526
```

```
<210> SEQ ID NO 2
<211> LENGTH: 1522
<212> TYPE: DNA
<213> ORGANISM: Burkholderia sp.
<220> FEATURE:
<221> NAME/KEY: 16S rDNA (16Sr RNA)
<222> LOCATION: (1)..(1522)

<400> SEQUENCE: 2
```

```
gagtttgatc ctggctcaga ttgaacgctg gcggcatgcc ttacacatgc aagtcgaacg      60
gcagcgcggg ggcaaccctg gcggcgagtg gcgaacgggt gagtaataca tcggaacgtg     120
tcctgtagtg ggggatagcc cggcgaaagc cggattaata ccgcatacgc tctacggagg     180
aaagggggga atcttaggac ctctcgctac aggggcggcc gatggcagat tagctagttg     240
gtggggtaaa ggcctaccaa ggcgacgatc tgtagctggt ctgagaggac gaccagccac     300
actgggactg agacacggcc cagactccta cgggaggcag cagtggggaa ttttggacaa     360
tgggcgcaag cctgatccag caatgccgcg tgtgtgaaga aggccttcgg gttgtaaagc     420
acttttgtcc ggaaagaaaa cgccgtggtt aatacccgtg gcggatgacg gtaccggaag     480
aataagcacc ggctaactac gtgccagcag ccgcggtaat acgtagggtg caagcgttaa     540
tcggaattac tgggcgtaaa gcgtgcgcag gcggtccgct aagacagatg tgaaatcccc     600
gggcttaacc tgggaactgc atttgtgact ggcgggctag agtatggcag agggggtag     660 aattccacgt gtagcagtga aatgcgtaga gatgtggagg aataccgatg gcgaaggcag     720 cccctggc caatactgac gctcatgcac gaaagcgtgg ggagcaaaca ggattagata     780
ccctggtagt ccacgcccta aacgatgtca actagttgtt ggggattcat ttccttagta     840
acgtagctaa cgcgtgaagt tgaccgcctg gggagtacgg tcgcaagatt aaaactcaaa     900
ggaattgacg gggacccgca caagcggtgg atgatgtgga ttaattcgat gcaacgcgaa     960
aaaccttacc taccttgac atgtatggaa tcctgctgag aggtgggagt gcccgaaagg    1020
gagccataac acaggtgctg catggctgtc gtcagctcgt gtcgtgagat gttgggttaa    1080
gtcccgcaac gagcgcaacc cttgtcccta gttgctacgc aagagcactc tagggagact    1140
gccggtgaca aaccggagga aggtgggat gacgtcaagt cctcatggcc cttatgggta    1200
gggcttcaca cgtcatacaa tggtcggaac agagggtcgc caaccgcga ggggagcca    1260 atcccagaaa accgatcgta gtccggatcg cactctgcaa ctcgagtgcg tgaagctgga    1320
atcgctagta atcgcggatc agcatgccgc ggtgaatacg ttcccgggtc ttgtacacac    1380
cgcccgtcac accatgggag tgggttttac cagaagtggc tagtctaacc gcaaggagga    1440
cggtcaccac ggtaggattc atgactgggg tgaagtcgta acaaggtagc cgtatcggaa    1500
ggtgcggctg gatcacctcc tt                                             1522
```

PROCESS FOR THE PRODUCTION OF β-AMINO ACIDS USING ACYLASE

This application is a divisional application under 35 U.S.C. §120 to U.S. patent application Ser. No. 11/198,242, filed Aug. 8, 2005, now U.S. Pat. No. 7,351,571, which claimed priority under 35 U.S.C. §119 to Japanese Patent Application No. 2004-231306, filed Aug. 6, 2004, the contents of both of which are incorporated by reference in their entireties. The Sequence Listing filed electronically herewith is also hereby incorporated by reference in its entirety (File Name: US-245D; File Size: 5 KB; Date Created: Oct. 26, 2007).

BACKGROUND OF THE INVENTION

1. Field of the Invention

The present invention relates to a process for the selective production of an S-β-amino acid or an R-β-amino acid by reacting a racemic compound of N-acetyl β-amino acid with an acylase having an asymmetric hydrolysis activity on the N-acetyl β-amino acid, and to novel microorganisms that may be used in the above process.

2. Background Art

β-amino acids are non-naturally occurring amino acids that are not components of animal proteins. Like other non-naturally occurring amino acids, the β-amino acids have been in demand more as intermediate compounds for medical products, and have been used as ingredients in some medical products (Chimica OGGI/Chemistry today 10, 15 (2002)).

The following three methods are already known for production of β-amino acids using acylase:

(1) Method with Penicillin G Acylase (Formula 1)

This method is most popular and is referred to in, for example, V. A. Soloshonok et al., Tetrahedron, 6, 1601 (1995) and the like. This method uses phenylacetylation of the amino group of a racemic compound such as 3-amino-3-phenylpropionic acid (referred to hereinafter as "β-phenyl alanine"), followed by division using Penicillin G acylase to selectively produce its R-form.

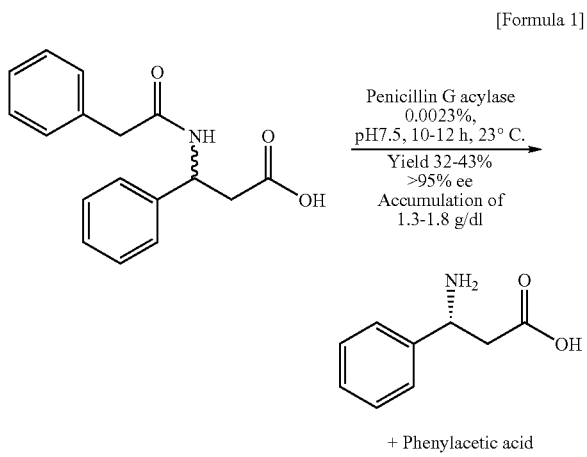

(2) Method with Porcine Kidney Acylase I (Formula 2)

The amino group of the racemic compound of β-phenylalanine is chloroacetylated and N-chloroacetyl-β-phenylalanine is divided using porcine kidney acylase I to selectively produce its S-form (WO2003/080854A2, published 02.10.1003, Degussa Co., or Grayson & K. Drauz CHIMICA OGGI/chemistry today 10, 5 (2002)). According to the specification, the reaction did not substantially occur when N-acetyl-β-phenylalanine was used.

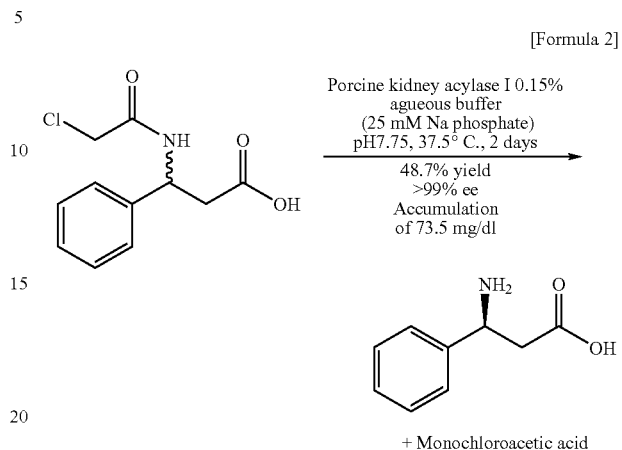

(3) Method with Glutaryl 7-aminocephalosporanic Adid Acylase (Formula 3)

The amino group of the racemic compound of β-phenylalanine is glutarylated and N-gluaryl-β-phenylalanine is divided using Glutaryl 7-aminocephalosporanic acid acylase to selectively produce its R-form (WO2003/020943A2, published 13. 03. 2003, Aventis Pharma).

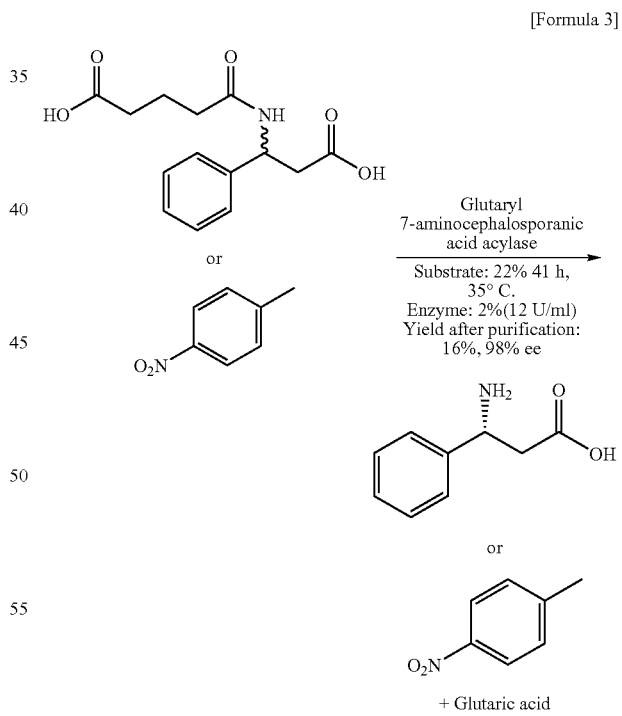

SUMMARY OF THE INVENTION

For normal α-amino acids, the amino group is generally acetylated followed by division using S- or R-selective acylase. However, no hydrolase has been described for N-acetyl-β-amino acids.

Acetylation is most commonly used since the N-acetyl group is readily formed by merely reacting an amino acid with acetic anhydride. However, as mentioned above, phenylacetylation, chloroacetylation, and glutarylation have been used for β-amino acids, since there is no acylase for hydrolyzing the N-acetyl group.

For solving the above problems, the present inventors have studied intensively and found novel microorganisms that produce an enzyme capable of selectively hydrolyzing the N-acetyl group to its S-form or R-form. The present inventors have further confirmed that the S-form or R-form of β-amino acids may be freely produced using these microorganisms, and have accordingly completed the present invention.

It is an object of the present invention to provide a *Variovorax* sp. strain which produces an acylase having an asymmetric hydrolysis activity on an N-acetyl β-amino acid so that an R-β-amino acid is selectively produced.

It is a further object of the present invention to provide the *Variovorax* sp. strain described above wherein the N-acetyl β-amino acid comprises N-acetyl β-phenylalanine.

It is an object of the present invention to provide the Strain 119L (AJ 110348, FERM ABP-10367).

It is an object of the present invention to provide a *Burkholderia* sp. strain which produces both an acylase having an asymmetric hydrolysis activity on an N-acetyl β-amino acid to selectively produce an S-β-amino acid, and an acylase having an asymmetric hydrolysis activity on an N-acetyl β-amino acid to selectively produce R-β-amino acid.

It is an object of the present invention to provide the *Burkholderia* sp. strain according to claim 4 wherein the N-acetyl β-amino acid comprises N-acetyl β-phenylalanine.

It is a further object of the present invention to provide the Strain 130F (AJ 110349, FERM ABP-10366).

It is an object of the present invention to provide a process for the selective production of an S-β-amino acid or an R-β-amino acid comprising reacting a racemic compound of N-acetyl β-amino acid with an acylase having an asymmetric hydrolysis activity on said N-acetyl β-amino acid.

It is an object of the present invention to provide a process for the selective production of an R-β-amino acid as described above comprising reacting a racemic compound of N-acetyl β-amino acid with an acylase having an asymmetric hydrolysis activity on the N-acetyl β-amino acid.

It is an object of the present invention to provide a process for the selective production of an S-β-amino acid by the strain as described above comprising reacting at a range of about 25~about 30° C. a racemic compound of N-acetyl β-amino acid with the acylase having an asymmetric hydrolysis activity on the N-acetyl β-amino acid.

A process for the selective production of an R-β-amino acid by the strain as described above comprising reacting at a range of about 75~about 80° C. a racemic compound of N-acetyl β-amino acid with an acylase having an asymmetric hydrolysis activity on the N-acetyl β-amino acid.

The process as described above, wherein the racemic compound of N-acetyl β-amino acid is added into a suspension of the strain so to react with the acylase.

The process as described above, wherein the racemic compound of N-acetyl β-amino acid is added into a supernatant of the strain breakage solution so to react with the acylase.

Thus, the present invention provides strains which produce an acylase having an asymmetric hydrolysis activity on an N-acetyl β-amino acid to selectively produce an S-, or R-β-amino acid.

DESCRIPTION OF THE PREFERRED EMBODIMENTS

Figure 1:
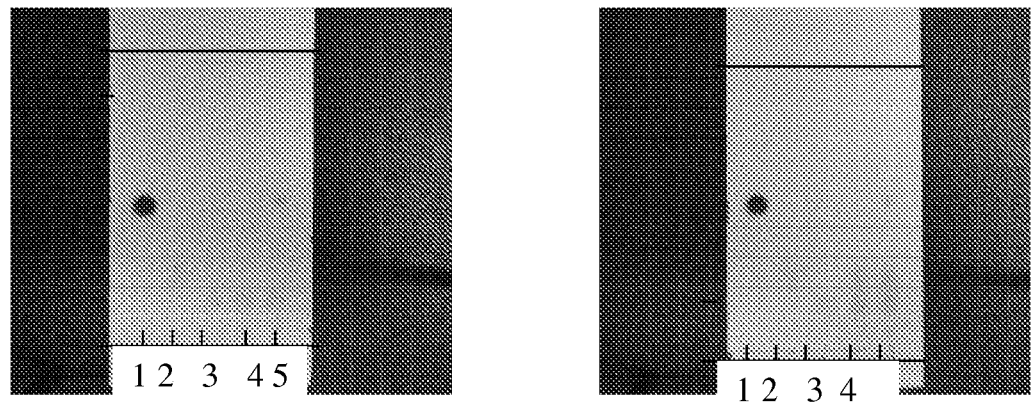
FIG. 1 shows photos of the electrophoresis, which show the production of β-Phe from N-acetyl-DL-β-Phe (Left: 119L; Right: 130F). 1: DL-β-Phe 0.5% solution, N-acetyl-DL-β-Phe 0.5% solution, 3: Reaction solution without the enzyme, 4: Time 0, 5: Time 3 hours.

*Variovorax* sp. of the present invention is characterized by producing an acylase having an asymmetric hydrolysis activity on an N-acetyl-β-amino acid to selectively produce an R-β-amino acid.

*Burkholderia* sp. of the present invention is characterized by producing both an acylase having an asymmetric hydrolysis activity on an N-acetyl β-amino acid to selectively produce an S-β-amino acid and an acylase having an asymmetric hydrolysis activity on an N-acetyl β-amino acid to selectively produce an R-β-amino acid. As demonstrated in the following examples, the optimal reaction temperature of an acylase to selectively produce the S-form ranges between about 25° C. and about 30° C., preferably around 30° C., and the optimal reaction temperature of an acylase to selectively produce the R-form ranges between about 75° C. and about 80° C., preferably around 75° C.

There is no limitation on the N-acetyl β-amino acid, which can be represented by the following formula 4:

[Formula 4]

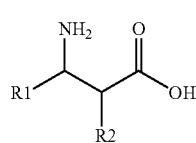

R1 can represent a C1-C6 alkyl group, a C6-C10 aryl group, a C7-C11 aralkyl group, or the same groups containing a hetero atom, which may have a substituent. R2 represents an hydrogen atom or hydroxy group. N-acetyl β-phenylalanine and its derivatives are preferred.

A strain that belongs to the *Variovorax* sp. of the present invention includes the strain 119L (AJ 110348), which was deposited on Jul. 22, 2004 at the International Patent Organism Depository, National Institute of Advanced Industrial Science and Technology and granted the number FERM AP-20129. This deposit was converted to a deposit under the Budapest Treaty on Jul. 4, 2005 and granted number FERM ABP-10367.

A strain that belongs to the *Burkholderia* sp. of the present invention includes the strain 130F (AJ 110349), which was deposited on Jul. 22, 2004 at the International Patent Organism Depository, National Institute of Advanced Industrial Science and Technology and granted the number FERM AP-20128. This deposit was converted to a deposit under the Budapest Treaty on Jul. 4, 2005 and granted number FERM ABP-10366.

Their mycological features are described in detail in the examples.

The reaction using the *Variovorax* sp. according to the present invention makes it possible to selectively hydrolyze the R-form of N-acetyl β-amino acid to produce R-β-amino acid while leaving N-acetyl(S)-β-amino acid.

The reaction using *Burkholderia* sp according to the present invention, for example, at a temperature of 30° C. makes it possible to selectively hydrolyze the S-form of N-acetyl β-amino acid to produce S-β-amino acid while leaving N-acetyl(R)-β-amino acid. On the other hand, the reaction with the same strain, for example, at a temperature of 75° C. makes it possible to selectively hydrolyze the R-form of N-acetyl β-amino acid to produce R-β-amino acid while leaving N-acetyl(S)-β-amino acid. Acetic acid is generated as a by-product.

The reaction scheme using N-acetyl-β-phenylananine as the N-acetyl β-amino acid is shown in formula 5 below.

For example, the racemic compound of N-acetyl β-amino acid may be added into the suspension of the strain or into the supernatant of the strain breakage solution so to react with the acylase.

The present invention will be explained more in detail with reference to the following non-limiting examples.

EXAMPLE 1

Chemical synthesis of N-acetyl-DL-3-amino-3-phenylpropionic acid (Ac-β-Phe)

β-Phe (45.3 g, manufactured by Aldrich) was mixed with 182 ml of water. Then, 32 ml of ice-cooled 25% sodium hydroxide aqueous solution was added to this mixture. The resulting solution was adjusted to pH 11.4. Acetic anhydride (58 ml) was dropped while being adjusted to pH 11~12 with 25% sodium hydroxide aqueous solution. The reaction solution was then heated to 40° C. and stirred for 3.5 hours while being adjusted to pH 11~12. After the reaction was complete, the insoluble matters were removed by filtration, and the

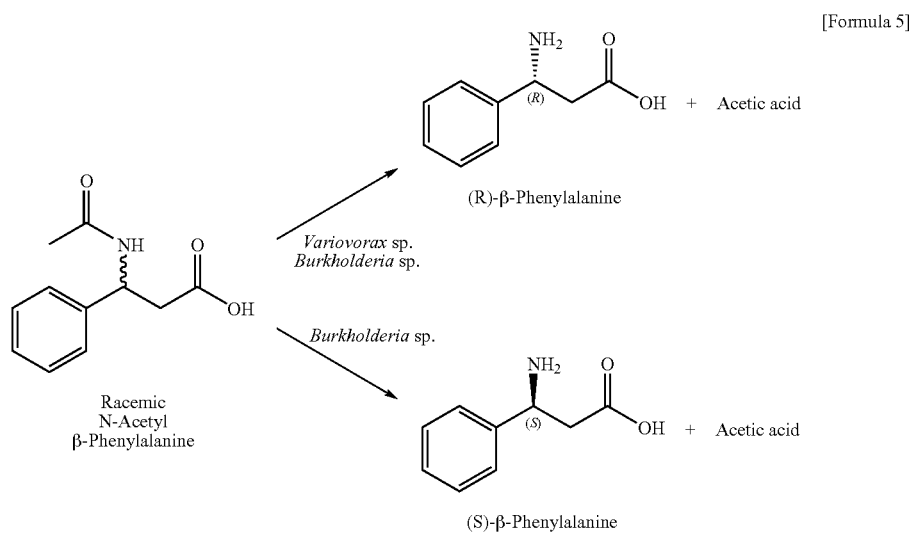

[Formula 5]

The present invention relates therefore to a process for the selective production of an S-β-amino acid or an R-β-amino acid by reacting a racemic compound of N-acetyl β-amino acid with an acylase having an asymmetric hydrolysis activity on the N-acetyl β-amino acids.

There is no limitation on the origin or preparation method of the acylase that is used in the above process, as long as it has the desired activity. Therefore, the acylase may be produced by the above strains, and prepared from the same strains by any method known to those skilled in the art. Alternatively, the enzyme produced by a recombinant host cell transformed by the gene encoding the acylase may also be utilized.

The manners, methods, conditions, and the like of the above reaction with the acylase in the present process may be optionally selected from those known to those skilled in the art depending on various conditions, such as the kind and amount of the acylase to be used, and production scale.

resulting filtrate was ice-cooled again. The solution was adjusted to pH 2 by adding 105 ml of conc. HCl followed by crystallization for 2 hours. The precipitated crystal was separated and washed with 100 ml of water. It was dried under reduced pressure at 40° C. to give a yield of 94% white crystals of Ac-β-Phe (53.4 g)

TLC analysis was carried out in the following examples by development on a silica gel 60F254 (Merck) with a developing solvent (butanol/acetic acid/water=4/1/2), and detection of the products by coloring with ninhydrin or absorbance at 254 nm. N-acetyl-DL-β-Phe prepared as above was used as the standard, N-acetyl-L-β-Phe (N-acetyl-(R)-β-Phe: prepared from L-β-Phe ((R)-β-Phe) manufactured by Watanabe Chemical Industry Inc. by the similar method), N-acetyl-D-β-Phe (N-acetyl-(S)-β-Phe: prepared from D-β-Phe ((S)-β-Phe) manufactured by Watanabe by the similar method), DL-β-Phe (Aldrich), L-β-Phe ((R)-β-Phe: Watanabe Chemical Industry Inc.), D-β-Phe ((RS)-β-Phe: Watanabe Chemical Industry Inc.).

EXAMPLE 2

Searching for β-Phe Acylase

A microorganism producing an enzyme that can hydrolyze the acetyl group of Ac-β-Phe with an optical specificity was screened in the following manner.

Screening of a microorganism having β-Phe aminoacylase:

Soil samples (200 samples) collected at various Kanto areas in Japan were inoculated into a synthetic culture medium (ammonium sulfate 10.0 g/l, $KH_2PO_4$ 1.0 g/l, $MgSO_4.7H_2O$ 0.4 g/l, $FeSO_4.7H_2O$ 10 mg/l, $MnSO_4.5H_2O$ 10 mg/, vitamin B1.HCl 0.2 mg/l, yeast extract 0.5 μl, N-acetyl-DL-β-Phe 5.0 g/l, pH8.0) containing chemically synthesized N-acetyl derivative of DL-β-Phe, and cultured with shaking. The enzyme reaction was done in the culture broth that showed growth of the microorganism.

The enzyme reaction was conducted by mixing one part 0.2 M phosphate buffer solution (pH 6.5) containing 1.0% N-acetyl-DL-β-Phe and one part the suspension of the strain or the supernatant of the strain breakage solution, and reacting for 3 hours at 31.5° C. After the reaction was terminated by incubating it for 5 min at 90° C., the reaction solution was analyzed by TLC analysis.

As a result, generation of β-Phe from N-acetyl derivative of DL-β-Phe was found in 4 samples. Microorganisms were isolated from the culture broth of these 4 samples, and a hydrolyzing activity of the DL-β-Phe derivatives was examined for the isolated strains. The microorganisms having β-Phe aminoacylase activity were successfully isolated from two strains (119L, 130F).

The mycological classification of the two strains was done by total base sequence analysis of 16SrDNA, and a homology search was conducted based on the total base sequence analysis (MicroSeq Microbial Full Library v.0001 (Applied Biosystems, CA, USA)), and molecular phylogenetic tree by proximate connection method (MicroSeq Microbial Identification Systgeneem Software V.1.4.1), which were consigned to NCIB Japan. In case any strain showing 100% identity in the homology search was not found, the classification was done by homology search using DNA base sequence data base (GenBank/DDBJ/EMBL) with BLAST. The total 16SrDNA sequences of the strains 119L and 130F are shown in Table 1, as Seq. ID N0.1, and in Table 2, as Seq. ID N0.2, respectively. Furthermore, their mycological features (morphological characters and physiological characters) are summarized in Table 3 and Table 4 (the strain 119L) and Table 5 and Table 6 (the strain 130F).

TABLE 1

| | |
|---|---|
| 1 | gagtttgatc ctggctcaga ttgaacgctg gcggcatgcc ttacacatgc |
| 51 | aagtcgaacg gcagcgcggg agcaatcctg gcggcgagtg gcgaacgggt |
| 101 | gagtaataca tcggaacgtg cccaatcgtg ggggataacg cagcgaaagc |
| 151 | tgtgctaata ccgcatacga tctacggatg aaagcagggg atcgcaagac |
| 201 | cttgcgcgaa tggagcggcc gatggcagat taggtagttg gtgaggtaaa |
| 251 | ggctcaccaa gccttcgatc tgtagctggt ctgagaggac gaccagccac |
| 301 | actgggactg agacacggcc cagactccta cgggaggcag cagtggggaa |
| 351 | ttttggacaa tgggcgcaag cctgatccag ccatgccgcg tgcaggatga |
| 401 | aggccttcgg gttgtaaact gcttttgtac ggaacgaaac ggctctttct |
| 451 | aataaagagg gctaatgacg gtaccgtaag aataagcacc ggctaactac |
| 501 | gtgccagcag ccgcggtaat acgtagggtg caagcgttaa tcggaattac |
| 551 | tgggcgtaaa gcgtgcgcag gcggtgatgt aagacagttg tgaaatcccc |
| 601 | gggctcaacc tgggaactgc atctgtgact gcatcgctgg agtacggcag |
| 651 | aggggatgg aattccgcgt gtagcagtga aatgcgtaga tatgcggagg |
| 701 | aacaccgatg gcgaaggcaa tcccctgggc ctgtactgac gctcatgcac |
| 751 | gaaagcgtgg ggagcaaaca ggattagata ccctggtagt ccacgcccta |
| 801 | aacgatgtca actggttgtt gggtcttcac tgactcagta acgaagctaa |
| 851 | cgcgtgaagt tgaccgcctg gggagtacgg ccgcaaggtt gaaactcaaa |
| 901 | ggaattgacg gggacccgca caagcggtgg atgatgtggt ttaattcgat |
| 951 | gcaacgcgaa aaaccttacc cacctttgac atgtacggaa tttgccagag |
| 1001 | atggcttagt gctcgaaaga gaaccgtaac acaggtgctg catggctgtc |
| 1051 | gtcagctcgt gtcgtgagat gttgggttaa gtcccgcaac gagcgcaacc |
| 1101 | cttgtcatta gttgctacat tcagttgggc actctaatga gactgccggt |
| 1151 | gacaaaccgg aggaaggtgg ggatgacgtc aagtcctcat ggcccttata |

TABLE 1-continued

```
1201  ggtggggcta cacacgtcat acaatggctg gtacaaaggg ttgccaaccc
1251  gcgaggggga gctaatccca taaaaccagt cgtagtccgg atcgcagtct
1301  gcaactcgac tgcgtgaagt cggaatcgct agtaatcgtg gatcagaatg
1351  tcacggtgaa tacgttcccg ggtcttgtac acaccgcccg tcacaccatg
1401  ggagcgggtt ctgccagaag tagttagctt aaccgcaagg agggcgatta
1451  ccacggcagg gttcgtgact ggggtgaagt cgtaacaagg tagccgtatc
1501  ggaaggtgcg gctggatcac ctcctt
```

TABLE 2

```
   1  gagtttgatc ctggctcaga ttgaacgctg gcggcatgcc ttacacatgc
  51  aagtcgaacg gcagcgcggg ggcaaccctg gcggcgagtg gcgaacgggt
 101  gagtaataca tcggaacgtg tcctgtagtg ggggatagcc cggcgaaagc
 151  cggattaata ccgcatacgc tctacggagg aaagggggg atcttaggac
 201  ctctcgctac aggggcggcc gatggcagat tagctagttg gtggggtaaa
 251  ggcctaccaa ggcgacgatc tgtagctggt ctgagaggac gaccagccac
 301  actgggactg agacacggcc cagactccta cgggaggcag cagtggggaa
 351  ttttggacaa tgggcgcaag cctgatccag caatgccgcg tgtgtgaaga
 401  aggccttcgg gttgtaaagc acttttgtcc ggaaagaaaa cgccgtggtt
 451  aatacccgtg gcggatgacg gtaccggaag aataagcacc ggctaactac
 501  gtgccagcag ccgcggtaat acgtagggtg caagcgttaa tcggaattac
 551  tgggcgtaaa gcgtgcgcag gcggtccgct aagacagatg tgaaatcccc
 601  gggcttaacc tgggaactgc atttgtgact ggcgggctag agtatggcag
 651  aggggggtag aattccacgt gtagcagtga atgcgtaga gatgtggagg
 701  aataccgatg gcgaaggcag ccccctgggc caatactgac gctcatgcac
 751  gaaagcgtgg ggagcaaaca ggattagata ccctggtagt ccacgcccta
 801  aacgatgtca actagttgtt ggggattcat ttccttagta acgtagctaa
 851  cgcgtgaagt tgaccgcctg gggagtacgg tcgcaagatt aaaactcaaa
 901  ggaattgacg gggacccgca caagcggtgg atgatgtgga ttaattcgat
 951  gcaacgcgaa aaaccttacc tacccttgac atgtatggaa tcctgctgag
1001  aggtggggagt gcccgaaagg gagccataac acaggtgctg catggctgtc
1051  gtcagctcgt gtcgtgagat gttgggttaa gtcccgcaac gagcgcaacc
1101  cttgtcccta gttgctacgc aagagcactc tagggagact gccggtgaca
1151  aaccggagga aggtggggat gacgtcaagt cctcatggcc cttatgggta
1201  gggcttcaca cgtcatacaa tggtcggaac agagggtcgc caacccgcga
1251  gggggagcca atcccagaaa accgatcgta gtccggatcg cactctgcaa
1301  ctcgagtgcg tgaagctgga atcgctagta atcgcggatc agcatgccgc
1351  ggtgaatacg ttccgggtc ttgtacacac cgcccgtcac accatgggag
1401  tgggttttac cagaagtggc tagtctaacc gcaaggagga cggtcaccac
```

TABLE 2-continued

```
1451  ggtaggattc atgactgggg tgaagtcgta acaaggtagc cgtatcggaa 1501  ggtgcggctg gatcacctcc tt
```

TABLE 3

| 1. Morphological characteristics: | |
| --- | --- |
| Culture conditions: | Nutrient agar (Oxoid, Hampshire, England) medium, 30° C. |
| Form of cell: | 0.6-0.7 × 1.5-2.0 μm |
| Polymorphism: | − |
| Mobility (the state of adherence of flagella): | + |
| Spore (site of spores): | − |
| 2. Culture characteristics: | |
| Culture conditions: | Nutrient agar (Oxoid, Hampshire, England) medium, 30° C. |
| Color: | Yellow |
| Luster: | + |
| Production of pigment: | + |
| Culture conditions: | Nutrient agar (Oxoid, Hampshire, England) medium, 30° C. |
| The presence of surface growth: | + |
| Turbidity of media: | + |
| Culture conditions: | Gelatin stab culture, 30° C. |
| State of growth: | − |
| Gelatin liquefaction[1]: | − |
| Culture conditions[2]: | Litmus milk, 30° C. |
| Coagulation: | − |
| Liquefaction: | − |
| 3. Physiological characteristics: | |
| Gram stain[1] | − |
| Reduction of nitrate[3] | − |
| Denitrification[2] | − |
| MR test[2] | − |
| VP test[3] | + |
| Production of indole[3] | − |
| Production of hydrogen sulfide[3] | − |
| Hydrolysis of starch[2] | − |
| Utilization of citric acid[2] (Koser) | + |
| Utilization of citric acid[2] (Christensen) | − |
| Utilization of inorganic nitrogen[2] (nitrate) | + |
| Utilization of inorganic nitrogen[2] (ammonium salt) | + |
| Catalase[2] | + |
| Oxidase[2] | + |
| Range of growth (pH 5): | + |
| Range of growth (pH 8): | + |
| Range of growth (pH10): | − |
| Range of temperature (20° C.): | + |
| Range of temperature (25° C.): | + |
| Range of temperature (37° C.): | +w |
| Range of temperature (45° C.): | − |
| Behavior toward anaerobic: | + |
| O-F test (Oxidation/Fermentation)[2]: | −/− |

TABLE 4

| 4. Formation of acids/gases[2] | |
| --- | --- |
| L-arabinose | −/− |
| D-xylose | −/− |
| D-glucose | −/− |
| D-mannose | −/− |
| D-fluctose | −/− |
| D-galactose | −/− |
| Maltose | −/− |
| Sucrose | −/− |

TABLE 4-continued

| Lactose | −/− |
| --- | --- |
| Trehalose | −/− |
| D-sorbiotl | −/− |
| D-mannitol | −/− |
| Inositol | −/− |
| Glycerin | −/− |
| 5. Other physiological characteristics:[3] | |
| β-Galactosidase activity: | − |
| Arginine dihydrolase activity: | − |
| Lysine decarboxylase activity: | − |
| Tryptophan deaminase activity: | − |
| Gelatinase activity: | − |

References and Kit
[1] BARROW, (G. I.) and FELTHAM, (R. K. A.): Cowan and Steel's Manual for the Identification of Medical Bacteria. 3rd edition, 1993, Cambridge University Press.
[2] Toshikazu Sakazaki et al., "New Lectures on Bacterial Culture," 2nd edition, 1988, Kindai Publisher, Tokyo
[3] Kit for identification of bacteria API20 NE (bioMerieux, France): http://www-.biomerieux.fr/home_en.htm)

TABLE 5

| 1. Morphological characteristics: | |
| --- | --- |
| Culture conditions: | Designated medium, 30° C. |
| Form of cell: | 0.5-0.6 × 1.0-1.5 μm |
| Polymorphism: | − |
| Mobility (the state of adherence of flagella): | + |
| Spore (site of spores): | − |
| 2. Culture characteristics: | |
| Culture conditions: | Designated medium, 30° C. |
| Color: | Cream |
| Luster: | + |
| Production of pigment: | − |
| Culture conditions: | Nutrient agar (Oxoid, Hampshire, England) medium, 30° C. |
| The presence of surface growth: | − |
| Turbidity of media: | + |
| Culture conditions: | Gelatin stab culture, 30° C. |
| State of growth: | − |
| Gelatin liquefaction[1]: | − |
| Culture conditions[2]: | Litmus milk, 30° C. |
| Coagulation: | − |
| Liquefaction: | − |
| 3. Physiological characteristics: | |
| Gram stain[1] | − |
| Reduction of nitrate[3] | + |
| Denitrification[2] | − |
| MR test[2] | − |
| VP test[3] | + |
| Production of indole[3] | − |
| Production of hydrogen sulfide[3] | − |
| Hydrolysis of starch[2] | − |
| Utilization of citric acid[2] (Koser) | + |
| Utilization of citric acid[2] (Christensen) | + |
| Utilization of inorganic nitrogen[2] (nitrate) | + |
| Utilization of inorganic nitrogen[2] (ammonium salt) | + |
| Urease activity[3] | − |
| Catalase[2] | + |
| Oxidase[2] | + |

TABLE 5-continued

| | |
|---|---|
| Range of growth (pH 5): | + |
| Range of growth (pH 8): | +w |
| Range of growth (pH10): | − |
| Range of temperature (20° C.): | +w |
| Range of temperature (25° C.): | + |
| Range of temperature (37° C.): | + |
| Range of temperature (45° C.): | − |
| Behavior toward anaerobic: | − |
| O-F test (Oxidation/Fermentation)[2]: | +/− |

TABLE 6

| 4. Formation of acids/gases[2] | |
|---|---|
| L-arabinose | +/− |
| D-xylose | +/− |
| D-glucose | −/− |
| D-mannose | −/− |
| D-fluctose | +/− |
| D-galactose | −/− |
| Maltose | +/− |
| Sucrose | −/− |
| Lactose | −/− |
| Trehalose | +/− |
| D-sorbiotl | −/− |
| D-mannitol | −/− |
| Inositol | −/− |
| Glycerin | −/− |
| 5. Other physiological characteristics:[3] | |
| β-Galactosidase activity: | + |
| Arginine dihydrolase activity: | − |
| Lysine decarboxylase activity: | − |
| Tryptophan deaminase activity: | − |
| Gelatinase activity: | − |

References and Kit
4) BARROW, (G. I.) and FELTHAM, (R. K. A.): Cowan and Steel's Manual for the Identification of Medical Bacteria. 3rd edition, 1993, Cambridge University Press.
5) Toshikazu Sakazaki et al., "New Lectures on Bacterial Culture, "2nd edition, 1988, Kindai Publisher, Tokyo
6) Kit for identification of bacteria API20 NE (bioMerieux, France: http://www-.biomerieux.fr/home_en.htm)

EXAMPLE 3

Determination of β-Phe Aminoacylase Activity

*Variovorax* sp. (FERM ABP-10367) or *Burkholderia* sp. (FERM ABP-10366) was inoculated into 20 ml of a culture medium (1% $(NH_4)_2SO_4$, 0.1% $KH_2PO_4$, 0.04% $MgSO_4 \cdot 7H_2O$, 10 ppm $FeSO_4 \cdot 7H_2O$, 10 ppm $MnSO_4 \cdot 7H_2O$, 0.2 ppm Vitamin B1 hydrochloride, 1% Glucose, 0.1% NaCl, 0.1% MES, 0.2% casamino acid, 0.5% N-acetyl-DL-β-Phe, pH7.0) in a shaking flask (500 ml) and cultured with shaking at 135 rpm and 31.5° C. for 24 or 48 hours. The strains were collected from the culture broth by centrifugation (8,000 ppm×15 min). A part of the collected strains was suspended in 0.2 M phosphate buffer (pH 6.5) and disrupted by ultrasonic treatment (300 W, 3.5 min, 4° C.). The disrupted strains were subjected to centrifugation (8,000 ppm×15 min) to remove the precipitate, giving supernatant of the strain breakage solution.

The enzyme reaction and TLC analysis as described above using the thus obtained strains and the supernatant of the strain breakage solution confirmed the enzyme activity in the strains and the supernatant. These results suggested that the enzymes were intracellular. As these enzymes were produced only when the strains were cultured in a medium containing the substrate, N-acetyl-DL-β-Phe, they were considered to be an inducible enzyme. The results are shown in FIG. 1.

EXAMPLE 4

Examination of the Substrate-Specificity of β-Phe Aminoacylase

Figure 2:
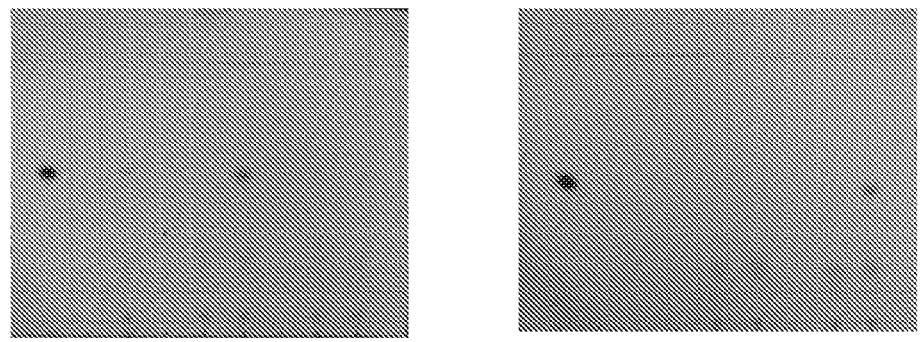
FIG. 2 shows photos of the electrophoresis, which shows the substrate specificity of β-Phe aminoacylase (Left: 119L; Right: 130F). 1: DL-β-Phe 0.5% solution, N-acetyl-DL-β-Phe 0.5% solution, 3: Before reaction, 4: Reaction solution of D-form, 5: D-form at time 0, 6: D-form at time 3 hours, 7: Reaction solution of L-form, 8: L-form at time 0, 9: L-form at time 3 hours.

The same enzyme reaction and TLC analysis were carried out using N-acetyl-L-β-Phe (N-acetyl-(R)-β-Phe) and N-acetyl-D-β-Phe (N-acetyl-(S)-β-Phe) instead of N-acetyl-DL-β-Phe (FIG. 2).

The results showed that *Variovorax* sp. (FERM ABP-10367) selectively hydrolyzed N-acetyl-L-β-Phe (N-acetyl-(R)-β-Phe) to produce only L-β-Phe ((R)-β-Phe) without any production of S-β-Phe, as seen from Table 7. All the data shown in Table 7 or herein after were determined by HPLC.

TABLE 7

| Time | Concentration (mM) | | | |
|---|---|---|---|---|
| (min) | N—Ac—R-β-Phe | N—Ac—S-β-Phe | R-β-Phe | S-β-Phe |
| 0 | 0.63 | 0.63 | 0.00 | 0.00 |
| 1 | 0.62 | 0.63 | 0.01 | 0.00 |
| 5 | 0.39 | 0.64 | 0.17 | 0.00 |
| 10 | 0.20 | 0.64 | 0.37 | 0.00 |
| 15 | 0.08 | 0.64 | 0.50 | 0.00 |
| 20 | 0.02 | 0.64 | 0.58 | 0.00 |
| 25 | 0.00 | 0.63 | 0.59 | 0.00 |
| 30 | 0.00 | 0.64 | 0.60 | 0.00 |

This data shows that the optimal pH range is between pH 7.5 and 8.0, as shown in Table 8. The results regarding the optimal reaction temperature are shown in Table 9 (reaction time: 10 min).

TABLE 8

| pH | R—N—Ac-β-Phe(mM) 0 min | R-β-Phe Production Ratio (mM) 10 min | Relative Activity (%) |
|---|---|---|---|
| 100 mM Na Acetate-HCl | | | |
| 3.5 | 0.63 | 0.00 | 0.00 |
| 4.0 | 0.50 | 0.00 | 0.00 |
| 5 | 0.57 | 0.00 | 0.00 |
| 5.5 | 0.56 | 0.00 | 0.00 |
| 100 mM MES-NaOH | | | |
| 5.5 | 0.62 | 0.00 | 0.00 |
| 6.0 | 0.48 | 0.05 | 26.3 |
| 6.5 | 0.44 | 0.08 | 40.2 |
| 7.0 | 0.32 | 0.13 | 61.5 |
| 100 mM Tris-HCl | | | |
| 7.0 | 0.35 | 0.14 | 71.0 |
| 7.5 | 0.29 | 0.20 | 100.00 |
| 8.0 | 0.29 | 0.20 | 96.0 |
| 9.0 | 0.42 | 0.07 | 34.3 |

TABLE 9

| Reaction Temperature (° C.) | R-β-Phe (mM) | Relative Activity (%) |
|---|---|---|
| 25 | 0.22 | 48.6 |
| 30 | 0.31 | 70.5 |
| 35 | 0.37 | 83.9 |
| 40 | 0.41 | 92.3 |

TABLE 9-continued

| Reaction Temperature (° C.) | R-β-Phe (mM) | Relative Activity (%) |
|---|---|---|
| 45 | 0.44 | 100 |
| 50 | 0.42 | 95.6 |
| 55 | 0.26 | 59.4 |
| 60 | 0.16 | 36.5 |
| 65 | 0.12 | 27.8 |
| 70 | 0.00 | 0.0 |
| 75 | 0.00 | 0.0 |

It was found that *Burkholderia* sp. (FERM ABP-10366) selectively hydrolyzed N-acetyl-D-β-Phe (N-acetyl-(S)-β-Phe) at 30° C. to produce only D-β-Phe ((S)-β-Phe), as seen from Table 10. The same reaction was then carried out for 15 min varying the reaction temperature, giving the results shown in Table 11.

TABLE 10

| Time (min)) | Concentration (mM) | | | |
|---|---|---|---|---|
| | N—Ac—R-β-Phe | N—Ac—S-β-Phe | R-β-Phe | S-β-Phe |
| 0 | 0.60 | 0.62 | 0.00 | 0.00 |
| 1 | 0.60 | 0.57 | 0.00 | 0.03 |
| 2 | 0.61 | 0.54 | 0.00 | 0.05 |
| 5 | 0.60 | 0.52 | 0.00 | 0.10 |
| 7 | 0.61 | 0.44 | 0.00 | 0.12 |
| 10 | 0.57 | 0.39 | 0.00 | 0.15 |
| 12 | 0.57 | 0.33 | 0.00 | 0.15 |
| 15 | 0.56 | 0.31 | 0.00 | 0.19 |
| 17 | 0.58 | 0.30 | 0.00 | 0.21 |
| 20 | 0.59 | 0.28 | 0.00 | 0.24 |
| 25 | 0.58 | 0.20 | 0.00 | 0.29 |
| 30 | 0.57 | 0.14 | 0.00 | 0.34 |
| 35 | 0.56 | 0.10 | 0.02 | 0.41 |
| 40 | 0.56 | 0.06 | 0.00 | 0.42 |
| 50 | 0.57 | 0.00 | 0.02 | 0.42 |

TABLE 11

| Reaction Temperature (° C.) | Concentration (mM) | | | |
|---|---|---|---|---|
| | N—Ac—R-β-Phe | N—Ac—S-β-Phe | R-β-Phe | S-β-Phe |
| 25 | 0.54 | 0.20 | 0.00 | 0.16 |
| 30 | 0.58 | 0.21 | 0.00 | 0.28 |
| 35 | 0.57 | 0.00 | 0.10 | 0.38 |
| 40 | 0.59 | 0.00 | 0.09 | 0.42 |
| 45 | 0.31 | 0.01 | 0.30 | 0.39 |
| 50 | 0.31 | 0.10 | 0.33 | 0.35 |
| 55 | 0.00 | 0.08 | 0.52 | 0.33 |
| 60 | 0.00 | 0.20 | 0.67 | 0.31 |
| 65 | 0.00 | 0.29 | 0.47 | 0.23 |
| 70 | 0.15 | 0.36 | 0.44 | 0.13 |
| 75 | 0.46 | 0.55 | 0.07 | 0.00 |
| 80 | 0.57 | 0.56 | 0.00 | 0.00 |

As seen from the results in Table 11, while S-β-Phe was selectively produced at the reaction temperature of 30° C. or below, R-β-Phe was selectively produced at the reaction temperature of 75° C. or above.

EXAMPLE 5

Reaction with Derivatives of β-Phenylalanine

The derivatives of β-phenylalanine and corresponding N-acetyl derivatives were prepared as follows, and the same experiments were done as above.

Synthesis of p-bromo-β-phenylalanine p-Bromo-benzaldehyde (10.0 g, 54 mmol) was mixed with 100 ml of ethanol/water (95/5), 8.3 g of ammonium acetate (108 mmol), and 11.2 g of malonic acid (108 mmol), heated under reflux at 80° C. with stirring for 17 hours, filtered under heating and dried under reduced pressure to give 8.3 g of p-bromo-β-phenylalanine crystals at a yield of 62.8%.

Synthesis of acetyl-p-bromo-β-phenylalanine p-Bromo-β-phenylalanine (10.0 g, 41 mmol) was mixed with 40 ml of water and adjusted to pH 14 with 25% sodium hydroxide aqueous solution. After being cooled to 5° C., 8.5 ml of acetic anhydride (90 mmol) and 25% sodium hydroxide aqueous solution were simultaneously dropped into the mixture to keep it at a pH range of 11.5~12 and the resulting mixture was stirred for 3 hours at a room temperature. After the mixture was adjusted to pH 2 with conc. HCl and stirred for one hour, the resulting precipitated crystal was filtered and dried under reduced pressure to give quantitatively 12.0 g of acetyl-p-bromo-β-phenylalanine.

Synthesis of p-nitro-β-phenylalanine

Acetic acid (110 ml) was mixed with 20.4 g of ammonium acetate (264 mmol) and heated to 85° C. After ammonium acetate was dissolved, the mixture was further mixed with 20.0 g of p-nitro-benzaldehyde (132 mmol) and 27.8 g of malonic acid (264 mmol) and heated at 90° C. with stirring for 5 hours. After being cooled to room temperature, the filtrate was mixed with 300 ml of 2-propanol. The precipitated crystal was filtered, subjected to slurry washing with 100 ml of ethanol, filtered again and dried under reduced pressure to give 14.4 g of p-nitro-β-phenylalanine at a yield of 52.0%.

Synthesis of acetyl-p-nitro-β-phenylalanine p-Nitro-β-phenylalanine (10.0 g, 48 mmol) was mixed with 40 ml of water and adjusted to pH 14 with 25% sodium hydroxide aqueous solution. After being cooled to 5° C., 10.7 ml of acetic anhydride (105 mmol) and 25% sodium hydroxide aqueous solution were simultaneously dropped into the mixture to keep it at a pH range of 11.5~12 and the resulting mixture was stirred for 1.5 hours at a room temperature. After the mixture was adjusted to pH 2 with conc. HCl and stirred for one hour, the resulting precipitated crystal was filtered and dried under reduced pressure to give 11.6 g of acetyl-p-nitro-β-phenylalanine at a yield of 96.9%.

Synthesis of 3,4-(—O—CH$_2$—O—)-β-phenylalanine

Piperonal (7.5 g, 50 mmol) was mixed with 75 ml of ethanol and 8.0 g of ammonium acetate (100 mmol), stirred at 40° C. and dissolved therein. To this solution 10.5 g of malonic acid (100 mmol) was added, and heated for 5 hours under reflux. After ethanol was concentrated under reduced pressure, the mixture was mixed with 75 ml of water and conc. HCl to adjust to pH2 and stirred for one hour. After the resulting precipitated crystal was filtered out, the filtrate was adjusted with 25% sodium hydroxide aqueous solution to pH6, mixed with 75 ml of methanol and stirred overnight. The resulting precipitated crystal was filtered, subjected to slurry washing with 25 ml of 2-propanol, filtered again, and dried under reduced pressure to give 4.6 g of 3,4-(—O—CH$_2$—O—)-β-phenylalanine at a yield of 43.5%.

Synthesis of acetyl-3,4-(—O—CH$_2$—O—)-β-phenylalanine 3,4-(—O—CH$_2$—O—)-β-phenylalanine (1.4 g, 7 mmol) was mixed with 28 ml of water and adjusted to pH 12 with 25% sodium hydroxide aqueous solution. After being cooled to 5° C., 1.6 ml of acetic anhydride (17 mmol) and 25% sodium hydroxide aqueous solution were simultaneously dropped into the mixture to keep it at a pH range of 11.5~12 and the resulting mixture was stirred for 2.5 hours at 40° C. After the mixture was filtered, the filtrate was adjusted to pH 2 with conc. HCl and stirred overnight. The resulting precipitated crystal was filtered and dried under reduced pressure to give 1.6 g of acetyl-1-3,4-(—O—CH$_2$—O—)-β-phenylalanine at a yield of 94.0%.

The reaction of N-acetyl compounds thus synthesized in the same way with *Variovorax* sp. (FERM ABP-10367) and *Burkholderia* sp. (FERM ABP-10366) as in Example 2 revealed that the same selective hydrolysis occurred.

Since N-acetyl compounds of β-amino acids may be used as a starting material in the process for the selective production of the S-β-amino acid or the R-β-amino acid in the present invention, this process has an advantage in view of cost compared to the conventional processes. Furthermore, as acetic acid generated as a by-product in the present process is a safe substance, it is also very environmentally favorable.

While the invention has been described in detail with reference to preferred embodiments thereof, it will be apparent to one skilled in the art that various changed can be made, and equivalents employed, without departing from the scope of the invention. All documents cited herein are hereby incorporated by reference.

What is claimed is:

1. A process for the selective production of an R-β-amino acid by an isolated *Variovorax* sp. strain comprising a 16SrDNA sequence of SEQ ID NO: 1, comprising reacting a racemic compound of N-acetyl β-amino acid with an acylase comprising an asymmetric hydrolysis activity on the N-acetyl β-amino acid.

2. A process for the selective production of an S-β-amino acid by an isolated *Burkholderia* sp. strain comprising a 16SrDNA sequence of SEQ ID NO: 2, comprising reacting at about 25° C. to about 30° C. a racemic compound of N-acetyl β-amino acid with an acylase comprising an asymmetric hydrolysis activity on the N-acetyl β-amino acid.

3. A process for the selective production of an R-β-amino acid by an isolated *Burkholderia* sp. strain comprising a 16SrDNA sequence of SEQ ID NO: 2, comprising reacting at about 75° C. to about 80° C. a racemic compound of N-acetyl β-amino acid with an acylase comprising an asymmetric hydrolysis activity on the N-acetyl β-amino acid.

4. A process of claim 1 wherein said racemic compound of N-acetyl β-amino acid is reacted with the acylase by adding it to a suspension of the strain.

5. The process of claim 2 wherein the racemic compound of N-acetyl β-amino acid is added into suspension of the strain so to react with the acylase.

6. The process of claim 3 wherein the racemic compound of N-acetyl β-amino acid is reacted with the acylase by adding it to a suspension of the strain.

* * * * *